United States Patent [19]

Drewes

[11] 4,169,952
[45] Oct. 2, 1979

[54] PROCESS FOR THE PREPARATION OF CYCLOHEXANONE-2-CARBOXAMIDE

[75] Inventor: Harold R. Drewes, Newark, Del.

[73] Assignee: E. I. Du Pont de Nemours and Company, Wilmington, Del.

[21] Appl. No.: 777,322

[22] Filed: Mar. 14, 1977

[51] Int. Cl.² .............. C07D 231/54; C07C 102/00
[52] U.S. Cl. .................. 548/359; 260/557 R; 544/253
[58] Field of Search ....... 260/557 R, 251 QA, 555 A, 260/555 B, 555 R; 548/359; 544/253

[56] References Cited

U.S. PATENT DOCUMENTS 2,104,348   6/1933   Lee et al. ............................ 548/359

FOREIGN PATENT DOCUMENTS 667356   7/1963   Canada ............................ 260/557 R
112987   5/1975   German Democratic Rep. ..... 260/557
961037   6/1964   United Kingdom ..................... 548/359
987597   3/1965   United Kingdom ..................... 548/359

Primary Examiner—Natalie Trousof
Assistant Examiner—Jane T. Fan

[57] ABSTRACT

This invention relates to an improved process for preparation of cyclohexanone 2-carboxamide which is in turn useful for preparing herbicides by condensation of one equivalent of urea with more than two equivalents of cyclohexanone, under controlled conditions of pH.

9 Claims, No Drawings

PROCESS FOR THE PREPARATION OF CYCLOHEXANONE-2-CARBOXAMIDE

BACKGROUND OF THE INVENTION

It is known that cyclohexanone 2-carboxamide is a valuable intermediate in the production of herbicides. As such, it is important that the carboxamide be readily available in high yield.

East German Pat. No. 112,987, published May 12, 1975, teaches the preparation of cyclohexanone 2-carboxamide by reaction of one equivalent of urea with 1 to 2 equivalents of cyclohexanone in the presence of an acid catalyst followed by acid hydrolysis. There is no teaching within the East German Patent of pH control during acid hydrolysis or the use of excess cyclohexanone. The utility of the carboxamide as an intermediate for preparation of herbicides is recognized.

Canadian Pat. No. 667,356 describes preparation of a spirolactam. It should be noted that an incorrect structure is assigned to the spirolactam in the Canadian Patent. The lactam is taught to be useful as an oxygen scavenger.

Because of the value of cyclohexanone 2-carboxamide as an intermediate for the preparation of herbicides, a process is needed for the preparation of carboxamide which will maximize product yield. According to the instant invention, such a process has been unexpectedly discovered.

SUMMARY OF THE INVENTION

According to the process of this invention, cyclohexanone-2-carboxamide is prepared according to the following equation:

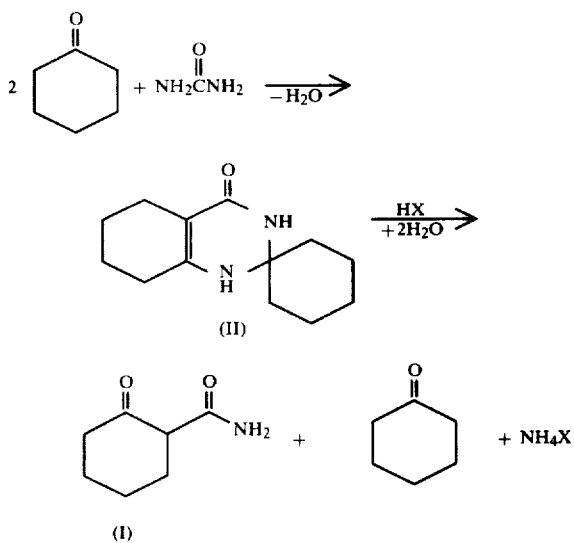

This process may be operated over a broad range of conditions. A stoichiometric excess of cyclohexanone is used; typically, molar ratios of cyclohexanone to urea of greater than 2:1 are used. Elevated temperatures such as temperatures of about 80° to 200° C. are used. Reaction time for the first (condensation) step may vary from about 1 to 24 hrs; and for the second (hydrolysis) step from about 0.3 to 4 hrs.; this will vary of course with the amount of II which is present. The hydrolysis step requires the presence of a mineral acid; a pH range of about 0.5 to 3.0 is critical during the hydrolysis.

The condensation step may be run in an organic solvent such as, but not limited to, xylene, toluene, decalin, Tenneco oil (a xylene-type solvent) or excess cyclohexanone. Ammonium salts may be added. Pressures are not critical.

Condensation Step

Two general cases categorize the condensation (first) step, and therefore the overall process: the use or lack of use of an organic solvent.

In a typical procedure when a solvent, such as xylene, decalin, toluene or Tenneco oil is used, a molar ratio of from about 2.04:1 to 4:1, preferably 2.04:1 to 3:1 of cyclohexanone to urea is used. The cyclohexanone is combined with the solvent and heated to about 100°-165° C., preferably to 130°-140° C., then the urea is added over about 5 to 60 min. An ammonium ion source such as ammonium carbonate or ammonium sulfate may be mixed with the urea prior to addition to suppress self-condensation of urea to form biuret. The resulting mixture is heated to reflux for 1 to 24 hours with the removal of water as an azeotrope with cyclohexanone and the solvent. After the evolution of water has ceased, the spirolactam II may be isolated by cooling and filtration, or the suspension may be slurried with water. The solvent and excess cyclohexanone may then be removed by steam distillation during or prior to the acid hydrolysis.

In a typical procedure when a solvent is not used, a ratio of cyclohexanone to urea of from 2.04:1 to 8:1, and preferably about 2.04:1 to 4:1 is used. The cyclohexanone is heated to about 125° to 155° C., preferably about 130° to 140° C., and the urea and ammonium salt are added over 5 to 60 min. The resulting mixture is heated to reflux for about 1 to 3 hrs until water evolution has ceased. The hot reaction mixture then is slurried in water.

Hydrolysis Step

The aqueous slurry of the spirolactam II is acidified with a mineral acid, such as hydrochloric or sulfuric acid, to a pH of about 0.5 to 3.0, preferably 0.8 to 2.3, or most preferably 1.4 to 2.0. Maintaining the pH in the designated range, the slurry is heated for about 0.3 to 4 hrs, preferably 0.3 to 1.0 hr, while the spirolactam is hydrolyzed and the cyclohexanone is removed by steam distillation. After removal of cyclohexanone is completed, pH of the solution is adjusted to about 4 to 6. The cyclohexanone -2-carboxamide may be isolated by crystallization from the aqueous solution. Preferably, it is retained in solution for use in a subsequent reaction.

Overall yields for the two-step process vary between about 55 and 80 percent, more typically between 60 and 75 percent.

pH control is essential to the instant invention; there must be continuous pH control during hydrolysis of spirolactam II, because it has unexpectedly been found that acid hydrolysis of II to yield cyclohexanone-2-carboxamide proceeds in high yield only if the pH is controlled between about 0.5 and 3.0, preferably between 0.8 and 2.3, and most preferably between 1.4 and 2.0.

The time of reaction for the first step is usually between about 1 and 24 hours, preferably between 1.5 and 3 hours. The time of reaction for the second (hydrolysis) step is usually between about 0.3 and 4 hours, preferably between 0.3 and 1.0 hour. Temperatures may vary widely depending upon solvent used (if any). Pressures are not critical and for economy and convenience ambient pressures are preferred.

DETAILED DESCRIPTION OF THE INVENTION

Initially, it has been found that at pH values above 3.0 spirolactam (II) is reasonably stable to hydrolysis thereby discouraging any formation of the desired cyclohexanone 2-carboxamide. The cyclohexanone-2-carboxamide is unstable at pH values below 0.5 and readily decomposes to cyclohexanone, carbon dioxide and ammonium salts.

It is a critical feature of the instant invention to continue adding acid during the course of the reaction to produce the carboxamide so as to control the acidity in a specific, narrow pH range. During the hydrolysis of the spirolactam (and the carboxamide as well) ammonia is liberated; the presence of this ammonia serves to neutralize some of the acid which is present. Thus, merely establishing an initial pH within the range of 0.5 to 3.0, preferably 0.8 to 2.3 and most preferably 1.4 to 2.0 is not sufficient. Incremental acid addition is needed for complete reaction.

In a preferred embodiment of this process, two equivalents (4 moles) of cyclohexanone are heated to about 135° to 140° C. and one equivalent (1 mole) of urea, mixed with 0.2 mole of ammonium carbonate, is added in portions. The resulting mixture is heated to reflux to remove water as an azeotropic mixture with cyclohexanone. Heating is discontinued when the evolution of water ceases. The hot mixture is slurried in 1100 parts of water at about 95° to 100° C. and acidified to a pH of about 0.8 to 2.3 using a mineral acid such as sulfuric acid. Maintaining the pH at 0.8 to 2.3, cyclohexanone is removed from the reaction mixture by steam distillation. The resulting solution is adjusted to a pH of about 5.0 with base (50 percent sodium hydroxide). The cyclohexanone-2-carboxamide solution may then be used in the preparation of an indazolone.

The following describes the preparation of cyclohexanone-2-carboxamide when solvent is present in this process.

Sixty parts of urea mixed with 18 parts of ammonium carbonate were added in portions to 200 parts of cyclohexanone in 100 parts of xylene at 135° C. The resulting mixture is refluxed to remove water as an azeotropic mixture with the solvent and cyclohexanone. Heating is discontinued when the water evolution has stopped. More solvent is added. The mixture is cooled, filtered and the solid washed with solvent to isolate the white crystalline spirolactam (II). This intermediate is slurried in 1100 parts of water and acidified to a pH of about 0.8 to 2.3 with a mineral acid, e.g. sulfuric acid. Maintaining the pH at 0.8 to 2.3, cyclohexanone is removed from the reaction mixture by steam distillation. The resulting solution is adjusted to a pH of 5.0 with base (50 percent sodium hydroxide). The cyclohexanone-2-carboxamide solution may then be used in the preparation of a hexahydroindazolone.

An aqueous slurry of one equivalent of an aromatic hydrazine acid addition salt, preferably an aromatic hydrazine hydrochloride (III), is stirred and heated at about 90° to 95° C. The pH is adjusted to about 3.8 to 4.0. An aqueous solution of one equivalent of cyclohexanone 2-carboxamide (I), preheated to about 90° to 95° C., is added over a period of about 3 to 10 minutes. After stirring at about 90° to 95° C. for about one-half to 4 hours, the resulting precipitate is filtered while hot, washed with toluene and dried to yield the hexahydroindazolone (IV).

More generally, the reaction takes place as follows:

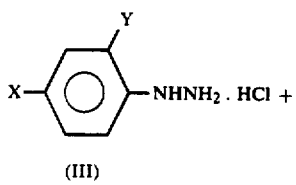

(III)

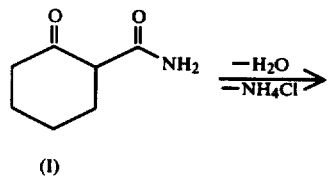

(I)

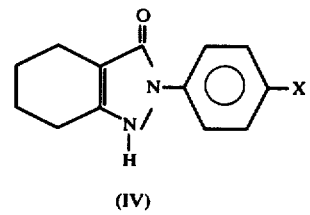

(IV)

where

Y is hydrogen, fluorine or chlorine; and

X is fluorine, chlorine, bromine, iodine, cyano, methoxy or nitro.

In the following examples all parts are by weight and all temperatures in degrees centigrade unless otherwise indicated. pH was measured with Colorphast 0–2.5 pH paper manufactured by E. M. Laboratories, Inc. pH is a measure of hydrogen ion concentration and therefore of acidity. One skilled in the art recognizes that measurements of pH colorimetrically with pH paper and electronically with a pH meter will not necessarily always be identical.

One skilled in the art will also recognize that pH values reported in the examples are in fact electrical potential difference readings and may be influenced by solvent composition, reagent concentration and temperature. The pH values would be expected to vary depending on specific reaction conditions. Nevertheless, these pH values are reproducible numbers which are extremely valuable for following the progress of the hydrolysis reaction. For a more extensive discussion of pH measurement, see Column 9, line 22 to Column 10, line 47 of U.S. Pat. No. 3,997,553 which is herein incorporated by reference.

EXAMPLE 1

Preparation of Cyclohexanone 2-Carboxamide Under Different Conditions

A. 60 Parts of urea were mixed with 18 parts of ammonium carbonate and were added in portions to 392 parts of cyclohexanone at 135°. The mixture was allowed to reflux with water continuously being separated with a Dean Stark trap. Water elimination was complete in 80 minutes; 36.5 parts of water were collected. Heating was discontinued and an aliquot was withdrawn. The product (370 parts) was poured into pans. It solidified quickly. Analysis using liquid chromatography showed 183.5 parts of spirolactam (yield=83%). 367 Parts of the crude product were added to 1150 parts of water at 99°, and the pH of the mixture was adjusted to 1.0 using 44 parts of 50% sulfuric acid. Cyclohexanone was removed from the mixture by steam distillation while maintaining a pH of 0.9–1.0 by dropwise addition of 155 parts of acid. 76 Parts of cyclohexanone were collected in 20 minutes, after which the pH of the reaction mixture was adjusted to 5 using sodium hydroxide. Analysis of the aqueous product (1337 parts) showed a concentration of 7.8% of cyclohexanone carboxamide. OVERALL YIELD DETERMINED BY LC ANALYSIS: 76%

B. 60 Parts of urea were mixed with 18 parts of ammonium carbonate and were added in portions to 200 parts of cyclohexanone in 100 parts of xylene at 135°. The mixture was allowed to reflux (at 138° to 142°) with water continuously separated using a Dean Stark trap. Water elimination was complete in four hours, with 32.5 parts of water collected. 130 Parts of xylene were added; the mixture was cooled, filtered and washed with xylene to isolate 174 parts of white crystalline product. Analysis by liquid chromatography showed the product to be 100% spirolactam (yield=79%). 166 Parts of this intermediate were slurried in 200 parts of warm water and acidified with 50% sulfuric acid in 100 parts of water and steam as in A. Analysis of the aqueous product (1523 parts) showed 5.1% cyclohexanone carboxamide. OVERALL YIELD DETERMINED BY LC ANALYSIS: 58%.

C. 60 Parts of urea were mixed with 18 parts of ammonium carbonate and this mixture added in portions to 200 parts of cyclohexanone in 100 parts of decalin at 135°. The mixture was refluxed (at 145° to 188°) with water continuously separated using a Dean Stark trap. Water elimination was complete in 1.8 hours, with 34 parts of water collected. 130 Parts of decalin were added; the mixture was cooled, filtered and washed with decalin to isolate 193 parts of crystalline product. Analysis by liquid chromatography showed the product to be 94.6% spirolactam (yield=83%). 186 Parts of this intermediate were slurried in 200 parts of warm water and processed with 50% sulfuric acid in 1150 parts of water and steam as in Example A. Analysis of the aqueous product (1662 parts) showed 5.0% cyclohexanone carboxamide. OVERALL YIELD DETERMINED BY LC ANALYSIS: 61%.

EXAMPLE 2 pH Dependency of Spiro Hydrolysis

A series of experiments were run to illustrate the critical pH range for hydrolyzing the spiro compound without hydrolyzing the ketoamide. This was done by using aqueous HCl solutions of 200 g volume containing 1.0 g of the spiro compound. The pH was controlled at a predetermined value for each of 12 pH values ranging from 0.05 to 4.0. The pH was measured by a pH probe immersed in the reaction mixture. A Corning Model 7 pH meter was used. A 5 ml aliquot was drawn from the hot solution at time 0, when the solid spiro compound was introduced into the acid solution at 95°±5° C., and at intervals of 10 minutes thereafter up to 60 minutes total reaction time. Each aliquot was immediately cooled to 10°–20° and a 2.00 ml aliquot drawn from it. The 2.00 ml aliquot was introduced into a tared flask and accurately weighed.

Analysis of ketoamide content was performed immediately by adding 25.00 ml of a solution containing an internal analytical standard, followed by injection into a high pressure liquid chromatograph. Weight percent of ketoamide in the reaction mixture was thus determined directly. The percent yield of ketoamide was calculated.

It is clear that at any reasonable reaction time, the yield of ketoamide is a function of pH. And to obtain a reasonable yield, the pH must be controlled within a specified region, e.g., 0.5 to 3.0. To obtain somewhat better yields, the pH must be restricted even further to the range 0.8 to 2.3. To obtain the best yields, the pH should be restricted to the range 1.4–2.0.

Operation outside these limits reduces the yield probably for either of 2 reasons:

(a) at low pH, below 0.5, because the ketoamide itself is being hydrolyzed rapidly.

(b) at higher pH, above 3.0, because the spiro compound does not hydrolyze at any appreciable rate.

These results dramatically demonstrate the criticality of pH control in this hydrolysis.

TABLE

SPIRO HYDROLYSIS
YIELD OF CYCLOHEXANONE-2-CARBOXAMIDE
AS A FUNCTION OF pH AND TIME

| pH | TIME (MIN) | | | | | | |
|---|---|---|---|---|---|---|---|
| | 0 | 10 | 20 | 30 | 40 | 50 | 60 |
| 0.05 | 5.6 | 20 | 3.4 | 0.3 | <0.3 | 0 | 0 |
| 0.6 | 40 | 76 | 66 | 56 | 47 | 41 | 35 |
| 0.8 | 16 | 76 | 76 | 66 | 60 | 56 | 51 |
| 1.0 | 12 | 79 | 77 | 77 | 69 | 69 | 64 |
| 1.2 | 16 | 76 | 78 | 78 | 76 | 75 | 72 |
| 1.4 | 5 | 65 | 79 | 80 | 81 | 79 | — |
| 1.6 | 11 | 75 | 90 | 92 | 89 | 87 | 85 |
| 2.0 | 1 | 42 | 78 | 89 | 86 | 85 | 86 |
| 2.3 | 0.6 | 19 | 46 | 69 | 72 | 87 | 79 |
| 2.7 | 0.3 | 8 | 19 | 32 | 45 | 58 | 57 |
| 3.0 | 0.3 | 7 | 13 | 22 | 29 | 40 | 46 |
| 4.0 | 0 | 0.6 | 1.6 | 3 | 4 | 5 | 6 |

What is claimed is:

1. In a process for preparing cyclohexanone 2-carboxamide consisting essentially of (1) condensing one equivalent of urea with a stoichiometric excess of cyclohexanone at an elevated temperature to form a spirolactam, and then (2) hydrolyzing the spirolactam to cyclohexanone 2-carboxamide, the improvement wherein the pH during the hydrolysis of the spirolactam is maintained between 0.8 and 2.3.

2. The process of claim 1 wherein the pH is maintained in a range of 1.4–2.0.

3. The process of claim 1 wherein there are at least 2.04 moles of cyclohexanone for each mole of urea.

4. The process of claim 1 wherein the condensation takes place in the presence of a solvent.

5. The process of claim 1 wherein the condensation takes place in the absence of a solvent.

6. The process of claim 1 wherein the cyclohexanone 2-carboxamide is then reacted with

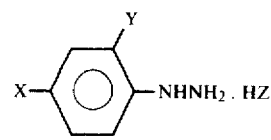

wherein:

Y is hydrogen, fluorine or chlorine; and

X is fluorine, chlorine, bromine, iodine, cyano, methoxy or nitro, and
Z is chloride or sulfate to form
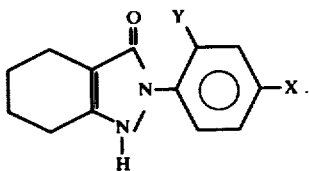
7. The process of claim 6 wherein Y is hydrogen and X is chlorine.
8. The process of claim 6 wherein Y is fluorine and X is chlorine.
9. The process of claim 6 wherein Y is fluorine and X is bromine.